US00PP32940P2

(12) United States Plant Patent
Smit

(10) Patent No.: US PP32,940 P2
(45) Date of Patent: Mar. 30, 2021

(54) ***PEPEROMIA* PLANT NAMED 'EC-PEPE-2008'**

(50) Latin Name: *Peperomia argyreia*
Varietal Denomination: EC-PEPE-2008

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/974,075

(22) Filed: Sep. 22, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden

(57) ABSTRACT

A new cultivar of *Peperomia* plant named 'EC-PEPE-2008' that is characterized by leaves that are grey-green on the upper surface with green areas surrounding the veins producing a watermelon like pattern and yellow-green on the lower surface, drop shaped leaves and a compact rosette like plant habit.

2 Drawing Sheets

Botanical classification: *Peperomia argyreia.*
Variety denomination: 'EC-PEPE-2008'.

BACKGROUND OF THE INVENTION

The present invention relates to a new and distinct cultivar of *Peperomia* plant botanically known as *Peperomia argyreia* and hereinafter referred to by the cultivar name 'EC-PEPE-2008'.

'EC-PEPE-2008' originated from the crossing of the female or seed parent, a proprietary *Peperomia argyreia* cultivar identified as 'meloenSmit' (not patented) and the male or pollen parent, a proprietary *Peperomia argyreia* cultivar identified as 'meloenIndo' (not patented). The crossing was conducted in 2015 in Sappemeer, Netherlands. The resulting seeds were subsequently planted and grown. The cultivar 'EC-PEPE-2008' was selected by the inventor in 2017 in a controlled environment as a single plant within the progeny of the stated cross in a cultivated area of Sappemeer, Netherlands.

Asexual reproduction of the new cultivar 'EC-PEPE-2008' first occurred by leaf cuttings in 2017 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'EC-PEPE-2008'. These traits in combination distinguish 'EC-PEPE-2008' as a new and distinct cultivar apart from other existing varieties of *Peperomia* known by the inventor.

1. *Peperomia* 'EC-PEPE-2008' exhibits leaves that are grey-green on the upper surface with green areas surrounding the veins producing a watermelon like pattern and yellow-green on the lower surface.
2. *Peperomia* 'EC-PEPE-2008' exhibits drop shaped leaves.

3. *Peperomia* 'EC-PEPE-2008' exhibits a compact rosette like plant habit.

The closest comparison cultivars are *Peperomia* 'Costa Rica' (U.S. Plant Pat. No. 32,128) and plants of the *Peperomia argyreia* species. 'EC-PEPE-2008' is distinguishable from 'Costa Rica' by the following characteristics:

1. *Peperomia* 'EC-PEPE-2008' exhibits leaves that are grey-green on the upper surface with green areas surrounding the veins producing a watermelon like pattern and yellow-green on the lower surface. In comparison, the leaves of 'Costa Rica' are green on the upper surface with silver-gray patches.
2. *Peperomia* 'EC-PEPE-2008' exhibits drop shaped leaves. In comparison, the leaves of 'Costa Rica' are heart shaped.
3. *Peperomia* 'EC-PEPE-2008' exhibits leaves that are larger than the leaves of 'Costa Rica'.
4. *Peperomia* 'EC-PEPE-2008' exhibits leaves having a rounded base. In comparison, the leaves of 'Costa Rica' have a hastate base with touching lobes forming an incision at the petiole.

'EC-PEPE-2008' is distinguishable from plants of the *Peperomia argyreia* species by the following characteristics:

1. *Peperomia* 'EC-PEPE-2008' exhibits a more compact and dense habit than plants of the *Peperomia argyreia* species. Plants of the *Peperomia argyreia* species have a less compact and more open habit.

'EC-PEPE-2008' is distinguishable from the female parent plant, by the following characteristics:

1. *Peperomia* 'EC-PEPE-2008' exhibits petioles that are shorter in length than the petioles of the female parent plant.

'EC-PEPE-2008' is distinguishable from the male parent plant by the following characteristics:

1. *Peperomia* 'EC-PEPE-2008' exhibits leaves that are larger than the leaves of the male parent plant.
2. *Peperomia* 'EC-PEPE-2008' exhibits petioles that are longer in length than the petioles of the male parent plant.

3. *Peperomia* 'EC-PEPE-2008' exhibits a smaller number of leaves than the number of leaves of the male parent plant.

BRIEF DESCRIPTION OF THE DRAWING

The accompanying photographs illustrate the distinguishing traits of *Peperomia* 'EC-PEPE-2008'.

The photograph of FIG. 1 shows an overall view of a 30 week old plant.

Figure 1:
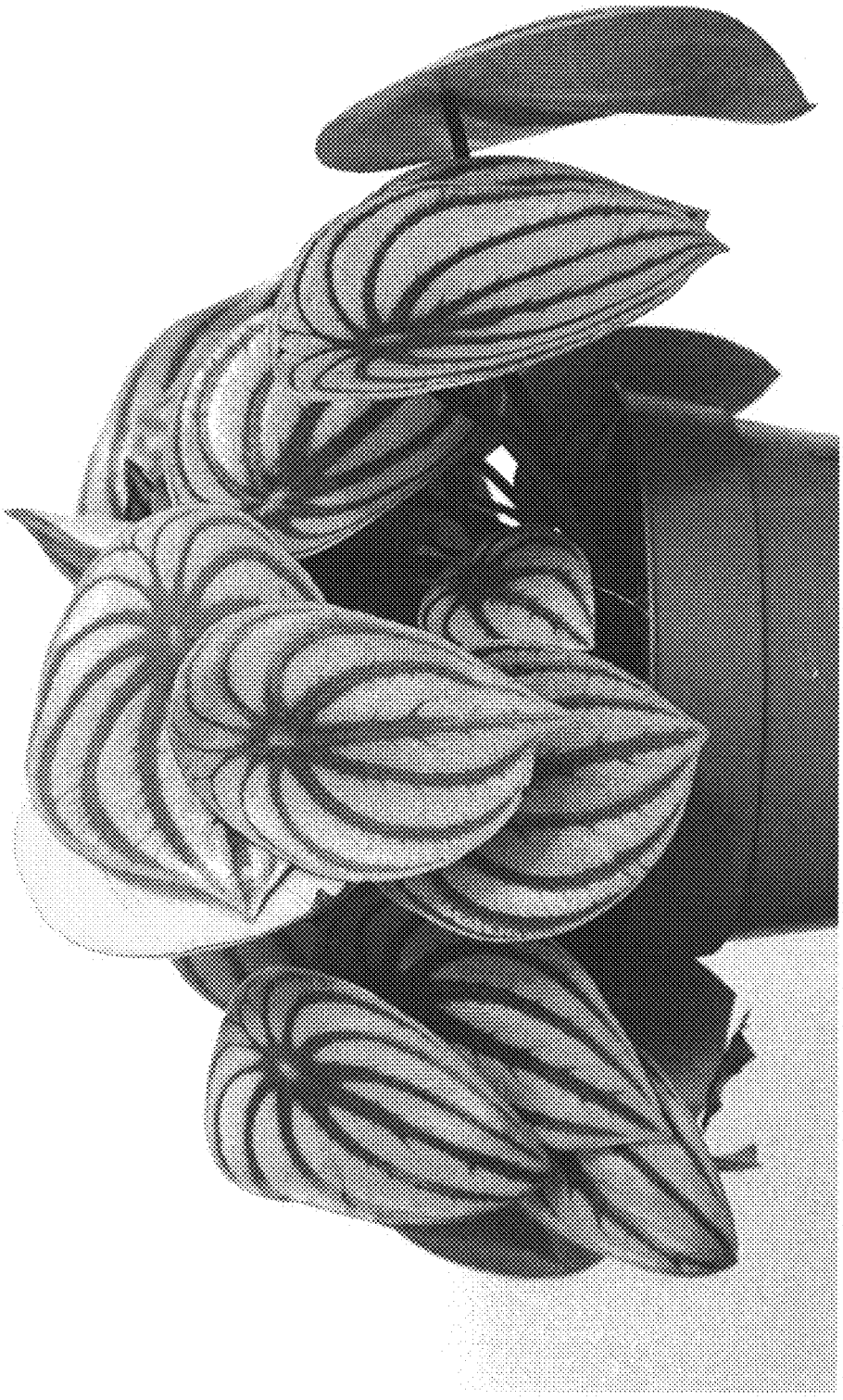
Figure 2:
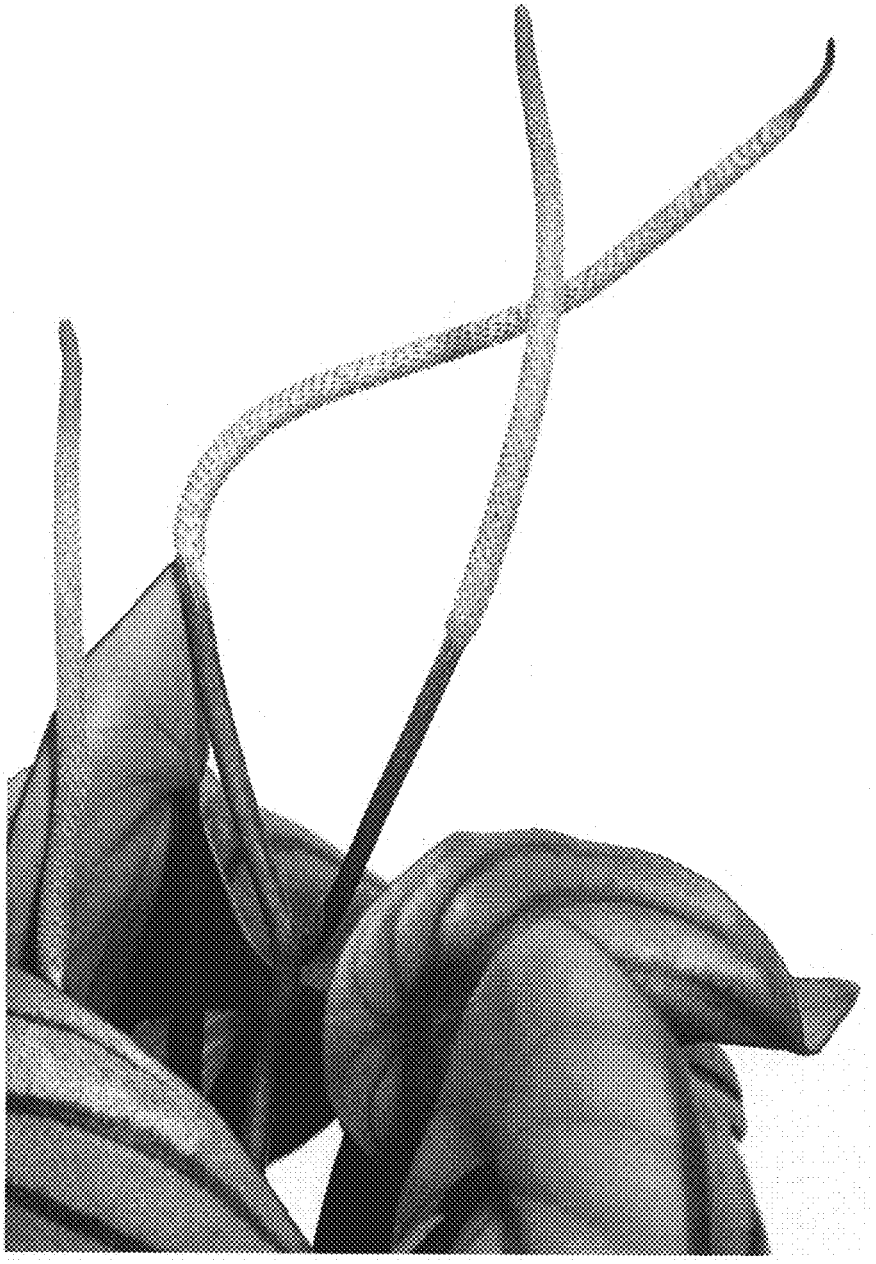

The photograph of FIG. 2 shows an enlarged view of the flowers.

The photographs were taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'EC-PEPE-2008'. Data was collected in Sappemeer, Netherlands from 30 week old plants grown in a glass greenhouse in 14 cm. diameter containers. The time of year was Spring and the temperature range was 20-23 degrees Centigrade during the day and 18-20 degrees Centigrade at night. The light level was natural light level with a shade screen in Spring/Summer. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-PEPE-2008' has not been tested under all possible conditions and phenotypic differences may be observed with variations in environmental, climatic, and cultural conditions, however, without any variance in genotype.

Botanical classification: *Peperomia argyreia* 'EC-PEPE-2008'.

Annual or perennial: Perennial.

Parentage: 'EC-PEPE-2008' is a hybrid of the female parent, *Peperomia* 'meloenSmit' and the male parent, *Peperomia* 'meloenIndo'.

Plant type: Potted plant.

Growth habit: Rosette of leaves, forming short thick stems.

Plant shape: Globe shaped with inflorescences carried slightly above the foliage plane.

Suitable container size: 11 cm. pots or larger.

Plant height to top of foliage: Average 18.3 cm.

Plant height to top of floral plane: Average 20.9 cm.

Plant width: Average 28.9 cm.

Vigor: Moderate.

Growth rate: Moderate.

Low temperature tolerance: 10° Centigrade.

High temperature tolerance: 40° Centigrade.

Propagation: Leaf cuttings.

Time to initiate roots (summer): 21 days at 20° C.

Time to initiate roots (winter): 28 days at 20° C.

Time to produce a rooted cutting (summer): 90 days at 20° C.

Time to produce a rooted cutting (winter): 110 days at 20° C.

Crop time: Approximately 30 weeks in Sappemeer, Netherlands.

Root system: Fibrous.

Plant fragrance: None.

Stem:

*Branching habit*.—Short thick main stems branching into rosettes of leaves, no lateral branches.

*Pinching*.—Not required.

*Number of main stems per plant*.—Average 7.

*Main stem dimensions*.—Average 3.5 cm. in length and 5.0 mm. in diameter.

*Internode length*.—Average 6.0 mm.

*Stem appearance*.—Succulent, moderately covered with lenticels, 2.0 mm. in length and 0.75 mm. in width, lenticel color 197C.

*Stem shape*.—Rounded.

*Stem luster*.—Moderately glossy.

*Stem pubescence*.—Absent.

*Stem angle*.—Average 45 degrees from vertical.

*Stem strength*.—Moderately strong.

*Stem color* (*young*).—183A.

*Stem color* (*mature*).—In between 183A and 200B.

*Internode color*.—In between 183A and 200B.

Foliage:

*Leaf arrangement*.—Alternate.

*Compound or single*.—Single.

*Quantity of leaves per branch*.—Average 6.

*Leaf shape*.—Broad ovate, perfoliate.

*Leaf aspect*.—Slightly concave.

*Leaf apex*.—Broad short apiculate.

*Leaf base*.—Rounded.

*Leaf dimensions*.—Average 11.2 cm. in length and 9.0 cm. in width.

*Leaf texture upper surface*.—Glabrous, slightly velvety, moderately leathery.

*Leaf texture lower surface*.—Glabrous, moderately leathery.

*Leaf luster upper surface*.—Glossy.

*Leaf luster lower surface*.—Slightly glossy.

*Pubescence*.—Absent (both surfaces).

*Leaf margin*.—Entire.

*Leaf lobed*.—Not lobed.

*Leaf rugose*.—Not rugose (both surfaces).

*Venation pattern*.—Parallel, slightly furrowed.

*Young leaf color* (*upper surface*).—144A, toward tip 145B.

*Young leaf color* (*lower surface*).—145A.

*Mature leaf color* (*upper surface*).—In between 191C and 194B, area surrounding veins in between NN137C and 141A.

*Mature leaf color* (*lower surface*).—147D to 148D.

*Vein color* (*upper surface*).—143A.

*Vein color* (*lower surface*).—146C.

Petiole:

*Petiole dimensions*.—Average 11.1 cm. in length and 5.0 mm. in diameter.

*Petiole texture*.—Glabrous.

*Petiole luster*.—Slightly glossy on both sides.

*Petiole pubescence*.—Absent.

*Petiole strength*.—Low.

*Petiole color*.—200B, tinged N186C.

*Petiole lenticels*.—Moderately covered with lenticels, less dense toward distal end, 2.0 mm. in length and 0.75 mm. in width, color 197C.

Flower:

*Inflorescence type*.—Axillary compound spike.

*Inflorescence dimensions*.—Average 7.0 cm. in length and 3.0 mm. in diameter.

*Quantity of flowers per inflorescence*.—Average 1000 per spike.

*Quantity of flowers per plant*.—Average 3000.
*Quantity of buds per plant*.—Average 3000.
*Quantity of flowers and buds per plant*.—Average 6000.
*Fragrance*.—None.
*Natural flowering season*.—Spring.
*Bud length*.—Average 0.4 mm.
*Bud diameter*.—Average 0.4 mm.
*Bud shape*.—Flattened orbicular.
*Bud texture*.—Glabrous, smooth, moderately velvety.
*Bud luster*.—Slightly glossy.
*Bud color*.—146D.
*Flower type and form*.—Flowers consist of one bract, two stamens and one pistil, no petals or sepals present.
*Flower aspect*.—Outward.
*Flower shape*.—Rotate, one bract, two stamens and one pistil.
*Flower dimensions*.—Average 0.5 mm. in diameter, 1.25 mm. in height, 0.4 mm. in depth.
*Flower longevity*.—Approximately 1 month.
*Persistent or self-cleaning*.—Self-cleaning.

Peduncle:
*Peduncle dimensions*.—Average 16.7 cm. in length and 3.0 mm. in diameter.
*Peduncle angle*.—Average 15 degrees from vertical.
*Peduncle strength*.—Weak.
*Peduncle texture*.—Glabrous, smooth.
*Peduncle luster*.—Slightly glossy.
*Peduncle color*.—183A with moderate fine stripes 197C.

Bracts:
*Bract arrangement*.—One flower bract is located below the stamens and pistil and two peduncle bracts are located at the peduncle axils.
*Flower bract dimensions*.—Average 0.4 mm. in length and 0.4 mm. in width.
*Flower bract shape*.—Orbicular.
*Flower bract color*.—147D.
*Peduncle bract dimensions*.—Average 1.1 cm. in length and 2.5 mm. in width.
*Peduncle bract shape*.—Lanceolate.
*Peduncle bract tip*.—Narrow acute.
*Peduncle bract base*.—Narrow cuneate.
*Peduncle bract color* (*both sides*).—148B, fading to 146B towards tip, base tinged 182C.

Reproductive organs:
*Stamen number*.—2.
*Anther shape*.—Kidney shaped.
*Anther length*.—Average 0.2 mm.
*Anther width*.—Average 0.15 mm.
*Anther color*.—199B.
*Filament length*.—Average 0.1 mm.
*Filament color*.—147D.
*Amount of pollen*.—Low.
*Pollen color*.—NN155A.
*Number of pistils*.—1.
*Pistil length*.—Average 0.2 mm.
*Stigma shape*.—Flattened, circular.
*Stigma dimensions*.—Average 0.1 mm. in length and 0.1 mm. in diameter.
*Stigma color*.—200B.
*Style*.—Not visible, stigma sessile.
*Ovary color*.—147D.

Fruit and seed: 'EC-PEPE-2008' has not produced fruit or seed to date.

Disease and pest resistance: Disease and pest resistance has not been observed.

The invention claimed is:

1. A new and distinct variety of *Peperomia* plant named 'EC-PEPE-2008' as described and illustrated.

* * * * *